United States Patent [19]

Egger et al.

[11] 4,107,164
[45] Aug. 15, 1978

[54] CERTAIN PLEUROMULILIN ESTER DERIVATIVES

[75] Inventors: Helmut Egger; Hellmuth Reinshagen, both of Vienna, Austria

[73] Assignee: Sandoz Ltd., Basel, Switzerland

[21] Appl. No.: 758,133

[22] Filed: Jan. 10, 1977

Related U.S. Application Data

[60] Division of Ser. No. 606,430, Aug. 21, 1975, Pat. No. 4,032,530, which is a division of Ser. No. 427,514, Dec. 26, 1973, Pat. No. 3,919,290, which is a continuation-in-part of Ser. No. 294,642, Oct. 3, 1972, abandoned.

[30] Foreign Application Priority Data

Oct. 5, 1971 [CH] Switzerland .................. 14450/71
Oct. 5, 1971 [CH] Switzerland .................. 14451/71
May 25, 1972 [CH] Switzerland .................. 7738/72
May 25, 1972 [CH] Switzerland .................. 7739/72
May 25, 1972 [CH] Switzerland .................. 7740/72

[51] Int. Cl.² .............. C07D 295/08; C07D 295/10; C07D 295/12; C07D 295/14
[52] U.S. Cl. .................................................. 544/380
[58] Field of Search .................. 260/239 BF, 268 TR

[56] References Cited

U.S. PATENT DOCUMENTS 3,919,290  11/1975  Egger et al. .................. 260/239 BF
4,032,530   6/1977  Egger et al. .................. 260/293.56

FOREIGN PATENT DOCUMENTS 2,036,027  2/1971  Fed. Rep. of Germany ...... 260/481 A Primary Examiner—Alton D. Rollins
Attorney, Agent, or Firm—Gerald D. Sharkin; Robert S. Honor; Thomas O. McGovern

[57] ABSTRACT

This invention relates to new pleuromutilins of the formula:

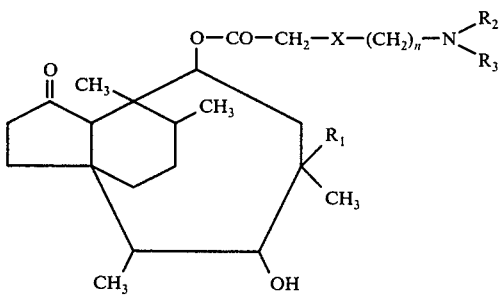

wherein
either
$R_1$ is ethyl or vinyl,
n is an integer from 2 to 5,
X is sulphur, a group

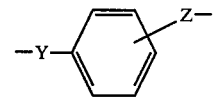

or a group $=N-R_4^I$, wherein
either Y and Z are both sulphur, or
one of Y and Z is oxygen and the other is sulphur, and
$R_4^I$ is hydrogen or a group of the formula:

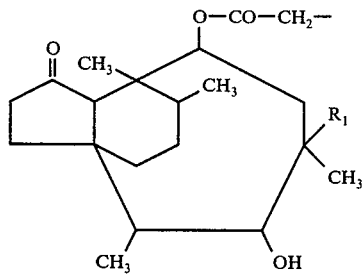

wherein
$R_1$ is as defined above,
each of
$R_2$ and $R_3$ is alkyl of 1 to 10 carbon atoms, or
$R_2$ and $R_3$ together with the nitrogen atom form a heterocycle of 5 to 7 ring members, and pharmaceutically acceptable acid addition salts and quaternary salts thereof.

Processes for the preparation of such compounds are described.

The compounds are antibiotics with an antibacterial effect.

31 Claims, No Drawings

CERTAIN PLEUROMULILIN ESTER DERIVATIVES

This is a division of application Ser. No. 606,430, filed Aug. 21, 1975, now U.S. Pat. No. 4,032,530, which in turn is a division of application Ser. No. 427,514, filed Dec. 26, 1973, now U.S. Pat. No. 3,919,209, which is a continuation-in-part of co-pending application Ser. No. 294,642, filed Oct. 3rd, 1972, now abandoned.

This invention relates to new pleuromutilins.

In accordance with the invention there are provided new pleuromutilins of formula I,

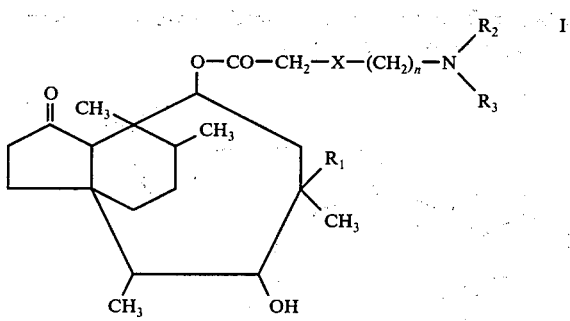

wherein
either
$R_1$ is ethyl or vinyl,
$n$ is an integer from 2 to 5,
$X$ is sulphur, a group

or a group $=N-R_4^I$,
wherein
either Y and Z are both sulphur, or
one of Y and Z is oxygen and the other is sulphur, and
$R_4^I$ is hydrogen or a group of formula II,

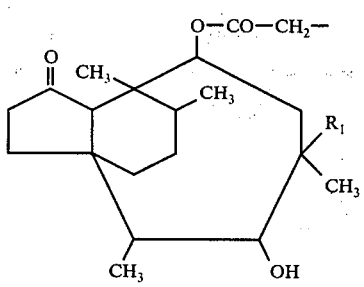

wherein
$R_1$ is as defined above, each of
$R_2$ and $R_3$ is alkyl of 1 to 10 carbon atoms, or
$R_2$ and $R_3$ together with the nitrogen atom form a heterocycle of 5 to 7 ring members containing one nitrogen atom or one nitrogen atom and a further hetero member selected from sulphur, oxygen and a group $=N-R_5^I$,
wherein $R_5^I$ is alkyl of 1 to 5 carbon atoms or hydroxyalkyl of 1 to 4 carbon atoms, or
$R_2$ and $R_3$ together with the nitrogen atom form a piperazinyl radical, the second nitrogen atom of which is substituted by a radical $R_5^{II}$,
whereby $R_5^{II}$ is (acyloxy of 2 to 5 carbon atoms)alkyl of 1 to 4 carbon atoms or (benzyloxy)alkyl of 1 to 4 carbon atoms,
or
wherein
$R_1$ is as defined above,
$n$ is the number 2,
$R_3$ is alkyl of 1 to 10 carbon atoms, hydroxyalkyl of 1 to 4 carbon atoms, (acyloxy of 2 to 5 carbon atoms)alkyl of 1 to 4 carbon atoms or (benzoyloxy)alkyl of 1 to 4 carbon atoms,
$X$ is the group $=N-R_4^{II}$, and
$R_2$ together with $R_4^{II}$ forms an ethylene bridge between both nitrogen atoms,
and acid addition salts and quaternary salts thereof.

Further, in accordance with the invention a compound of formula I and acid addition salts and quaternary salts thereof may be obtained by processes comprising
(a) reacting a compound of formula III,

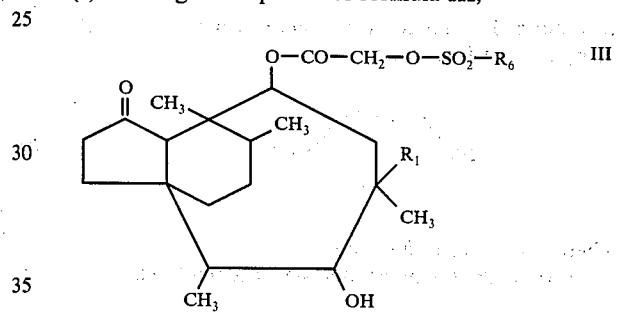

wherein
$R_1$ is as defined above, and
$R_6$ is alkyl or aryl,
with a compound of formula IV,

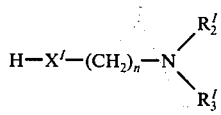

wherein
$n$ is as defined above.
$X^I$ is sulphur or a group

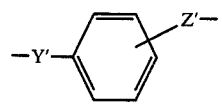

wherein Y' and Z' have the same significance as Y and Z, defined above,
provided Z is sulphur, and each of
$R_2^I$ and $R_3^I$ is alkyl of 1 to 10 carbon atoms, or
$R_2^I$ and $R_3^I$ together with the nitrogen atom form a heterocycle of 5 to 7 ring members containing one nitrogen atom or one nitrogen atom and a further hetero member selected from sulphur, oxygen and a group $=N-R_5^I$,
wherein $R_5^I$ is as defined above, to produce a pleuromutilin of formula Ia,

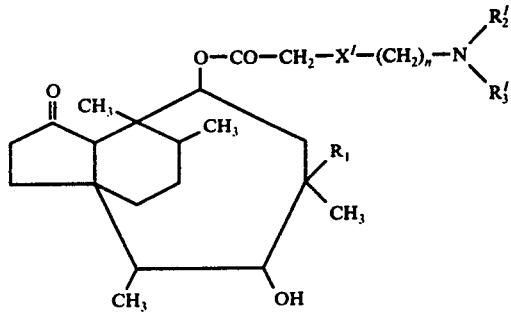

wherein $R_1$, $n$, $X^I$, $R_2^I$ and $R_3^I$ are as defined above, or (b) reacting a compound of formula III, indicated above, either with a compound of formula V,

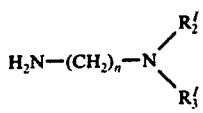

wherein $n$, $R_2^I$ and $R_3^I$ are as defined above, or with a compound of formula Va,

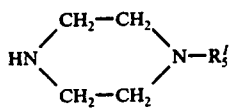

wherein $R_5^I$ is as defined above, (1) to produce a pleuromutilin of formula Ib,

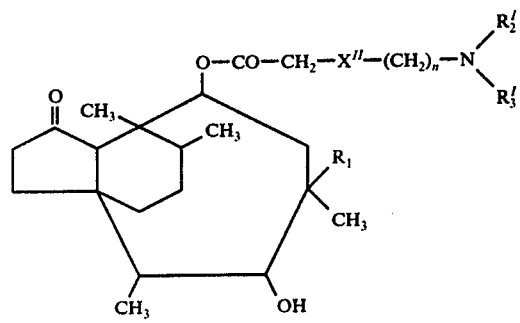

wherein $R_1$, $n$, $R_2^I$ and $R_3^I$ are as defined above, and $X^{II}$ is the group $=N-R_4^I$,
wherein $R_4^I$ is as defined above, or (2) to produce a pleuromutilin of formula Ib',

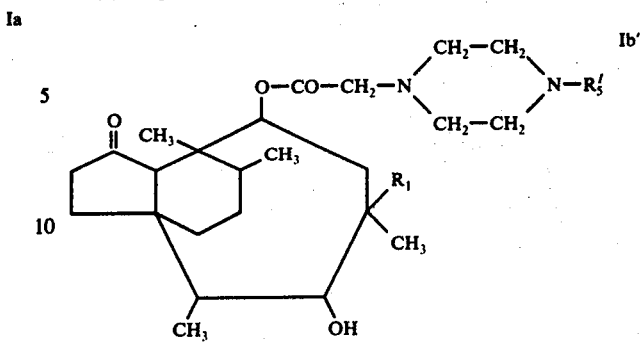

wherein $R_1$ and $R_5^I$ are as defined above, or c) reacting a compound of formula IIIa,

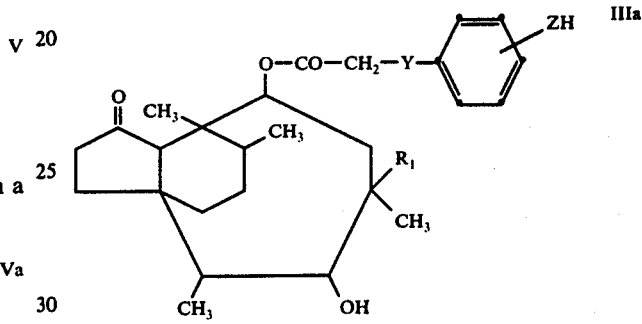

wherein $R_1$, Y and Z are as defined above, with a compound of formula VI,

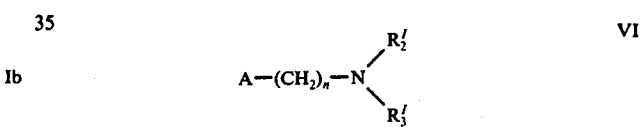

wherein
$n$, $R_2^I$ and $R_3^I$ are as defined above, and
A is the acid radical of a reactive ester,
to produce a pleuromutilin of formula Ic,

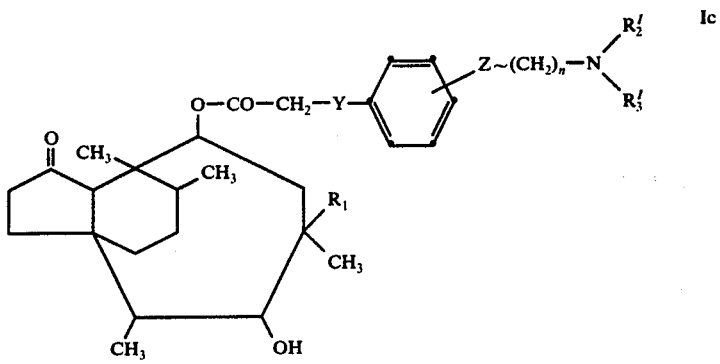

wherein $R_1$, $n$, $R_2^I$, $R_3^I$, Y and Z are as defined above or
d) reacting a compound of formula Ie,

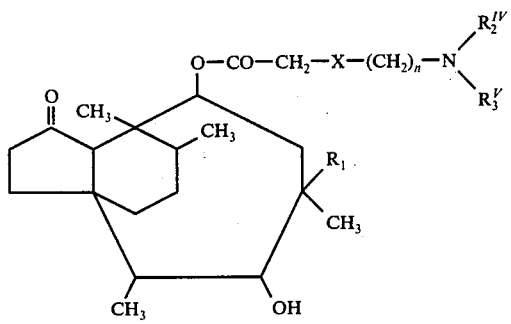

wherein
R$_1$, X and n are as defined above, R$_2^{IV}$ and R$_3^V$ together with the nitrogen atom form a piperazinyl radical, the second nitrogen atom of which is substituted by a radical R$_5^{III}$, whereby R$_5^{III}$ is hydroxy-alkyl of 1 to 4 carbon atoms, or reacting a compound of formula Ie',

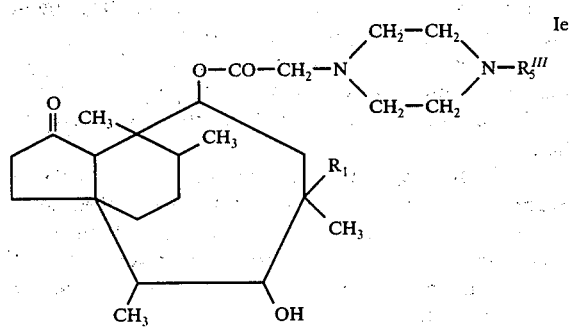

wherein R$_1$ and R$_5^{III}$ are as defined above, with a compound of formula VII, $$R_7-B \qquad \text{VII}$$

wherein
B is alkoxycarbonyl, chloro- or bromo-formyl, or a group R$_7$—CO—O—CO—, and
R$_7$ is alkyl of 1 to 4 carbon atoms or phenyl,
(1) to produce a pleuromutilin of formula Id,

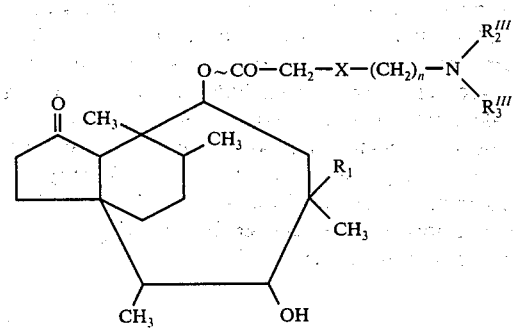

wherein
R$_1$, n and X are as defined above,
and
R$_2^{III}$ and R$_3^{III}$ together with the nitrogen atom form a piperazinyl radical, the second nitrogen atom of which is substituted by a radical R$_5^{II}$, as defined above, or
(2) to produce a pleuromutilin of formula Id',

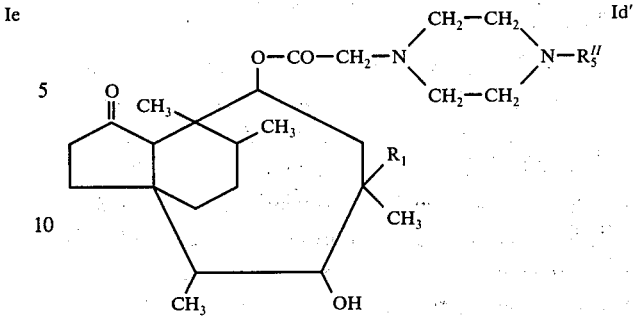

wherein R$_1$ and R$_5^{II}$ are as defined above, and, if desired, converting the resulting compounds of formula I into an acid addtion salt or quaternary salt.

Process a) may, for example, be effected by dissolving an acid addition salt of a compound of formula IV, e.g. a hydrohalide, or the free base in a solution of sodium in an anhydrous lower alcohol, e.g. ethanol. A solution of a compound of formula III in an inert solvent, e.g. an aliphatic ketone such as ethylmethyl ketone or acetone, is then added to this solution. The reaction is preferably effected at a temperature between room temperature and the boiling temperature of the reaction mixture, especially at 25° to 55° C. The reaction time under preferred conditions is from 2 to 12 hours. The process may suitably be carried out under an inert atmosphere, eg. nitrogen. R$_6$ in the compound of formula III may be, for example, alkyl of 1 to 6 carbon atoms or benzyl, although a wide variety of radicals may be used.

Process b) may, for example, be effected by adding a solution of a compound of formula III in an inert solvent, e.g. a lower aliphatic ketone such as ethylmethyl ketone or acetone, to a compound of formula V or Va. An acid-binding agent, e.g. a tertiary base such as triethylamine or pyridine, is conveniently added to the reaction mixture, and the reaction is conveniently carried out at an elevated temperature, preferably at the boiling temperature of the reaction mixture. The reaction usually has a duration of several hours and is generally concluded after 6 to 12 hours. When the reaction is effected with a primary amine, i.e. with a compound of formula V, then condensation products from one mol of a compound of formula V with one or two mols of a compound of formula III are preponderantly formed, depending on the reaction conditions (mol ratio of the reactants, reaction temperature and duration, addition and kind of reactant used, etc.), i.e. compounds of formula Ib wherein R$_4$ is hydrogen in the case of a mol ratio of 1:1, and R$_4$ is the radical of formula II in the case of a mol ratio of 1:2, result. Any mixtures of the two condensation products which may be obtained may be separated in known manner.

Process c) may, for example, be effected by dissolving a compound of formula IIIa in an inert solvent, e.g. an aliphatic ketone such as ethylmethyl ketone, or in a lower alcohol such as methanol or ethanol, subsequently adding a compound of formula VI, and allowing the reaction mixture to react, optionally in the presence of a base, e.g. an alkali metal carbonate such as potassium carbonate.

The reaction is preferably effected at a temperature between room temperature and the boiling temperature of the reaction mixture and has a duration, e.g., of 2 to 20 hours.

Process d) may, for example, be effected by allowing a compound of formula Ie or Ie' to react in a solvent with an acid derivative of formula VII for some time. Preferably the acid derivative is used as solvent alone or in admixture with an inert solvent, e.g. a chlorinated hydrocarbon such as dichloromethane. The reaction product may be isolated from the reaction mixture in known manner and optionally purified.

The compounds of formula I may be converted into their acid addition salts and vice versa.

The corresponding quaternary salts may be obtained from the compounds of formula I in accordance with known methods.

The alkyl groups represented by the symbols $R_2$ and $R_3$ or $R_2{}^I$ and $R_3{}^I$ preferably contain 1 to 8 carbon atoms; the lower alkyl groups represented by $R_5{}^I$ — preferably contain 1 to 3 carbon atoms.

The lower hydroxyalkyl groups represented by $R_3$, — $R_5{}^I$ and $R_5{}^{III}$ preferably contain two carbon atoms.

The lower acyloxy group contained in $R_3$ or $R_5{}^{II}$ preferably signifies the acetyl group.

The lower alkyl groups contained in the acyloxyalkyl or benzoyloxyalkyl radicals of $R_3$ — or $R_5{}^{II}$ preferably contain 2 carbon atoms. The number n preferably denotes 2 or 3.

The starting materials of formula IIIb,

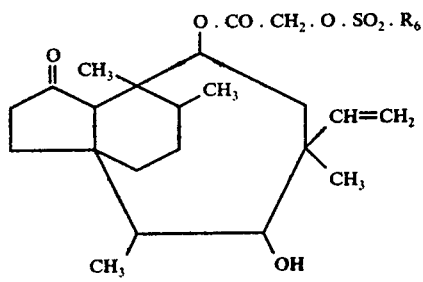

wherein $R_6$ is as defined above;
are known.

The starting materials of formula IIIc,

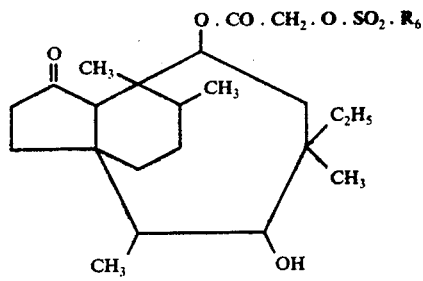

wherein $R_6$ is as defined above, may be obtained by
(α) reacting the compound of formula VIII

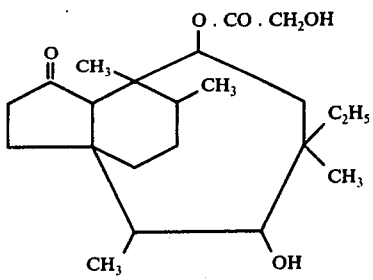

with a compound of formula IX, $$A-SO_2-R_6 \qquad IX$$

wherein A and $R_6$ are as defined above, or
(β) reducing a compound of formula IIIb.

The reaction in accordance with process α) can be effected in an inert solvent, e.g. an aromatic hydrocarbon such as toluene or benzene, preferably, however, in a solvent simultaneously acting as acidbinding agent, e.g. pyridine. p-Toluene sulphochloride may, for example, be used as compound of formula IX. The reaction may, for example, be effected at a temperature between $-15°$ and $-10°$ C and has a duration between 2 and 4 hours.

The hydrogenation of a compound of formula IIIb in accordance with process β) is conveniently effected by the action of hydrogen in the presence of a hydrogenation catalyst, e.g. a palladium or platinum charcoal catalyst, in an inert solvent, e.g. ethyl acetate, and at room temperature.

The starting materials of formula IIIa may be obtained by reacting a compound of formula III with a compound of formula X,

wherein Y and Z are as defined above, and Me is an alkali metal.

For example, the process is effected by reacting a compound of formula III with a compound of formula X in an inert water-miscible solvent, e.g. a lower aliphatic ketone such as acetone or methylethyl ketone, or in a lower alcohol such as methanol or ethanol, optionally in the presence of water or a water-immiscible inert organic solvent, e.g. dimethyl formamide, whereby the reaction temperature should amount to 20° to 60° C, preferably, however, to between 20° and 50° C.

The compounds of formula IVa,

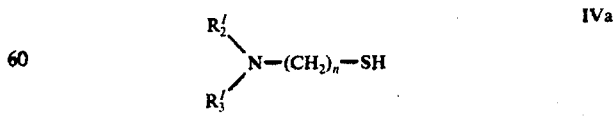

wherein n, $R_2{}^I$ and $R_3{}^I$ are as defined above, may be obtained by reaction of a compound of formula VI with thiourea and subsequent alkaline hydrolysis of the resulting complexes.

The compounds of formula IVb,

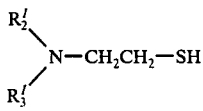

IVb wherein $R_2'$ and $R_3'$ are as defined above, may also be produced by reaction of a compound of formula XI,

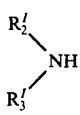

XI wherein $R_2'$ and $R_3'$ are as defined above, with ethylene sulphide.

The compounds of formula IVc,

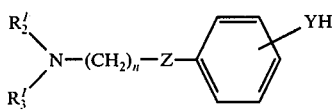

IVc wherein $R_2'$, $R_3'$, n, Z and Y are as defined above, may be obtained by reaction of a compound of formula VI with a compound of formula Xa,

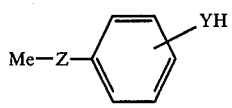

Xa wherein Z, Y and Me are as defined above.

Insofar as the production of the starting materials is not particularly described, these are known or may be produced in accordance with known processes, or in a manner analogous to the processes described herein or to known processes.

The compounds of formula I are useful because they possess pharmacological activity in animals. In particular the compounds are useful as antibiotics with an antibacterial action, as indicated by tests in vitro with the agar plate test, in which an inhibiting effect was obtained at a concentration of approximately 0.002 to 5 μg/ml, and in vivo tests in mice infected with different strains of bacteria, on subcutaneous or oral administration of 6 to 103 mg/kg animal body weight of the compound, and by inhibition tests with mycoplasms at concentrations of approximately 0.008 to 2.5 μg/ml. Action against the organisms Streptococcus aronson, Streptococcus haem., Staphylococcus aureus, M. arthritidis, M. bovigenitalium, M. bovimastitidis, M. bovirhinis, M.sp., M. canis, M. felis, M. fermentans, M. gallinarum, M. gallisepticum, A. granularum, M. hominis, M. hyorhinis, A. laidlawii, M. meleagridis, M. neurolyticum, M. pneumonia and M. hyopneumoniae is specifically indicated.

For the above-mentioned use, the dosage administered will, of course, vary depending upon the compound employed, mode of administration and treatment desired. However, in general, satisfactory results are obtained when administered at a daily dosage of from about 5 to 100 mg/kg animal body weight, conveniently given in divided doses two to four times a day, or in sustained release form. For the larger mammals, the total daily dosage is in the range of from about 50 to 1000 mg, and dosage forms suitable for oral administration comprise from about 10 to 500 mg of the compound admixed with a solid or liquid pharmaceutical carrier or diluent.

The compounds of formula I are indicated for the prophylaxis or therapy of microorganism infections in domestic animals, especially in pigs and poultry and are conveniently administered in feedstuffs or in drinking water. The dosage will of course vary depending upon the size and age of the animal and the effect desired; for example for prophylactic treatment relatively low doses would be administered over a long time. Preferred doses in drinking water are from 0.001 to 0.1% weight by volume, particularly 0.025 to 0.075%, and in foodstuffs from 100 to 1000 g/metric ton, particularly 200 to 600 g/ton. It is preferred to administer the active compound to hens in drinking water, and to pigs in the foodstuff.

Compounds which exhibit particularly interesting activity are 14-desoxy-14-{[2-(4-methyl)piperazino] ethylmercaptoacetoxy}mutilin and 14-desoxy-14-{[(2-hydroxyethyl)piperazino]ethylmercaptoacetoxy}mutilin. These compounds are active in tests in bacterially infected mice at dosages of 5 to 100 mg/kg animal body weight and are active as additives to drinking water for chickens at a concentration of 0.05 and 0.10% weight by volume.

The compounds of formula I may be administered in pharmaceutically acceptable acid addition or quaternary ammonium salt form. Such salt forms possess the same order of activity as the free bases and are readily prepared in conventional manner. Suitable such salt forms include salts with organic acids such as maleic, fumaric or tartaric acid, with mineral acids such as hydrochloric, hydrobromic or sulphuric acid, and with quaternizing agents such as methyl chloride or iodide.

The invention also provides a pharmaceutical composition comprising a compound of formula I, in free base or in pharmaceutically acceptable acid addition salt or quaternary ammonium salt form, in association with a pharmaceutically acceptable carrier or diluent. A suitable pharmaceutical form is a capsule, or a sterile injectable or instillation solution, containing the active compound.

In the following non-limitative Examples all temperatures are indicated in degrees Centigrade.

EXAMPLE 1:
14-Desoxy-14-[(2-dimethylaminoethyl)mercaptoacetoxy]mutilin ([process a)]

2.70 g of dimethylaminoethanethiol hydrochloride, which has been dried over phosphorus pentoxide, are added portionwise in an atmosphere of nitrogen to a solution of 1.40 g of sodium in 50 cc of absolute ethanol. 10.60 g of 14-desoxy-14-tosyloxyacetoxymutilin are subsequently dissolved in 30 cc of ethylmethyl ketone while heating and are added dropwise with stirring. The reaction mixture is stirred at room temperature for 4 hours and at 50°–55° for 30 minutes. The mixture is then concentrated almost to dryness, the residue is dissolved in ethyl acetate, and the product is converted into the aqueous phase as hydrochloride by extracting with 3 portions of 2 N hydrochloric acid. The base may again be extracted therefrom with ethyl acetate after adjusting the pH to 11 by the addition of sodium hydroxide. The ethyl acetate solution is washed twice with water, dried over magnesium sulphate and concentrated by evaporation in a vacuum.

The hydrochloride is obtained therefrom by concentrating by evaporation with methanolic hydrochloric acid in a vacuum or by taking up in methylene chloride, adding an equivalent amount of ethereal hydrochloric acid and concentrating by evaporation in a vacuum. After drying over potassium hydroxide the compound has a softening point of 95°.

The trimethyl ammonium iodide is produced by boiling at reflux 870 mg of 14-desoxy-14-[(2-dimethylaminoethyl)mercaptoacetoxy]mutilin in 15 cc of methanol with 3 cc of methyl iodide for 1 hour. The solution is then strongly concentrated, ether is added until it become turbid, and it is strongly cooled. Precipitation is completed by further addition of ether, the precipitate is filtered with suction, is thoroughly washed with ether and dried over phosphorus pentoxide. Softening point 150°–160°.

For the production of the trimethyl ammonium chloride, an ion exchange resin columm with 120 g of anion exchange resin (Cl$^-$ form, grain size 0.15–0.3 mm) is washed with distilled water until no chloride can be detected in the eluate. The eluate is sucked to dryness, reduced to slime thrice with a mixture of methanol and methylene chloride (4:1) and washed. 35 g of the trimethyl ammonium iodide are dissolved in 300 cc of the above solvent mixture and are slowly allowed to drop through the exchange resin column. The solvent is evaporated, whereby the trimethyl ammonium chloride is obtained (iodine content < 0.2%). As opposed to the trimethyl ammonium iodide, it is slightly water-soluble. M.P. 146–150°.

EXAMPLE 2:
14-Desoxy-14-[(2-piperidinoethyl)mercaptoacetoxy]-mutilin [process a)]

0.63 g of sodium are dissolved in 50 cc of absolute ethanol, 2.17 of piperidinoethanethiol hydrochloride are added in portions to the ethylate solution in an atmosphere of nitrogen, and then 6.4 g of 14-desoxy-14-tosyloxyacetoxymutilin, dissolved in 30 cc of ethylmethyl ketone, are added dropwise. The reaction mixture is stirred at room temperature for 4 hours. Working up is effected as described in Example 1. The crude product is purified by chromatography on silica gel with a mixture of methanol/chloroform (2:1) and is converted into the hydrochloride with hydrochloric acid in methanol; after triturating with ether and drying, the hydrochloride has a softening point of 88°–92°.

EXAMPLE 3:
14-Desoxy-14-[(2-diethylaminoethyl)mercaptoacetoxy]dihydromutilin [process a)]

5.35 g of 14-desoxy-14-tosyloxyacetoxydihydromutilin are dissolved in 15 cc of warm ethylmethyl ketone, and the solution is added dropwise in an atmosphere of nitrogen to a well stirred solution of 1.70 g of diethylaminoethanethiol hydrochloride in a previously prepared sodium ethylate solution (from 650 mg of sodium in 25 cc of absolute ethanol). After stirring at room temperature for 4 hours and heating to 50°–55° for 30 minutes, working up is effected as described in Example 1. The hydrochloride has a softening point of 45°–48°.

The diethylmethyl ammonium iodide may be obtained in a manner analogous to that described in Example 1. Softening point 115°–118°.

EXAMPLE 4:
14-Desoxy-14-[(2-diethylaminoethyl) mercaptoacetoxy]mutilin [process a)]

1.30 g of sodium are dissolved in 50 cc of absolute ethanol. 3.40 g of finely pulverized diethylaminoethanethiol hydrochloride, dried over phosphorus pentoxide, are added portionwise to the resulting solution in an atmosphere of nitrogen. A solution of 10.60 g of 14-desoxy-14-tosyloxyacetoxymutilin in 30 cc of ethylmethyl ketone is subsequently added dropwise while stirring. The reaction solution is stirred at room temperature for a further 4 hours, is subsequently kept at 50°–55° for 30 minutes and is then concentrated almost to dryness. The residue is taken up in ethyl acetate and the base is extracted therefrom with 3 portions of 2 N hydrochloric acid. The base is again taken up in ethyl acetate from the aqueous phase which has been rendered alkaline (pH 11) with sodium hydroxide. The ethyl acetate layer is finally washed twice with water, dried over sodium sulphate and concentrated by evaporation in a vacuum.

The hydrochloride, having a softening point of about 100°, and the diethylmethyl ammonium iodide, having a softening point of 110°–115°, may be obtained in a manner analogous to that described in Example 1. 30 g of crude 14-deoxy-14-[(2-diethylaminoethyl)mercaptoacetoxy]mutilin is dissolved in 50 ml of ether. This solution is admixed with a solution of 8.5 g fumaric acid in 100 ml of warm methanol (about 30° to 40), and the mixture carefully concentrated under vacuum. Upon dilution with portions of a mixture of ether and petroleum ether (2:1), crystallization of the salt takes place rapidly, and this is completed by storing in a refrigerator for 8 to 12 hours. After suction filtration and washing with ether/petroleum ether, the product is dried over silica gel at 20° under vacuum. The hydrogen fumarate is in the form of the methanol solvate. The product can be freed from solvent by pulverisation followed by drying at 80° under vacuum, to give a product of m.p. from 110° to 115° C.

EXAMPLE 5:
14-Desoxy-14-[(2-morpholinoethyl)mercaptoacetoxy]-mutilin [process a)]

A sodium ethoxide solution is prepared from 0.21 g of sodium and 20 cc of absolute ethanol, and 0.80 g of morpholinoethanethiol hydrochloride are then added portionwise in an atmosphere of nitrogen. A solution of 2.12 g of 14-desoxy-14-tosyloxyacetoxymutilin in 10 cc of ethylmethyl ketone is added dropwise to this mixture while stirring, and stirring is continued at room temperature for 12 hours. The mixture is then strongly concentrated in a vacuum, ethyl acetate and 2 N hydrochloric acid are added, and after separating the layers extraction is again effected twice with 2 N hydrochloric acid. The hydrochloric acid solution is then made alkaline with sodium hyroxide, and the precipitated free base is taken up in ethyl acetate. The ethyl acetate solution, which has been dried over magnesium sulphate, is concentrated by evaporation in a vacuum. Purification is effected by chromatography on silica gel with a mixture of chloroform/methanol (1:1) by eluant.

EXAMPLE 6:
14-Desoxy-14-[(2-diethylaminoethyl)mercaptoacetoxy]mutilin [process a)]

10.0 g of sodium are first dissolved in 350 cc of absolute methanol, and after cooling, 24.0 g of well dried diethylaminoethanethiol hydrochloride are added portionwise to the solution in an atmosphere of nitrogen. A solution of 79.5 g of 14-desoxy-14-tosyloxyacetoxymutilin in 250 cc of ethylmethyl ketone is subsequently added dropwise while stirring. After stirring at room temperature for 4 hours, the reaction solution is concentrated almost to dryness in a vacuum, is taken up in ethyl acetate and carefully washed with ice water. The ethyl acetate solution is then dried over magnesium sulphate and concentrated by evaporation in a vacuum. The residue of the crude base is dissolved in 80 cc of methylene chloride, and 40 cc of 5.8 N hydrochloric acid in ether are added. The solvent is evaporated, the evaporation residue is taken up in 120 cc of methanol, the solution is poured into 700 cc of distilled water and is extracted 5 times with a total of 700 cc of ether. The aqueous solution of the hydrochloride, which is homogeneous in accordance with thin layer chromatography, is filtered and then concentrated in a vacuum at a bath temperature of approximately 30°, whereby a foamy product is obtained, which is dried in a vacuum at 60° over potassium hydroxide.

EXAMPLE 7:
14-Desoxy-14-[(2-diisopropylaminoethyl)mercaptoacetoxy]mutilin [process a)]

1.54 of diisopropylaminoethanethiol are added to a solution of 0.35 g of sodium in 25 cc of absolute ethanol in an atmosphere of nitrogen. A solution of 5.33 g of 14-desoxy-14-tosyloxyacetoxymutilin in 15 cc of ethylmethyl ketone is added dropwise, stirring is effected for 5 hours at room temperature, and the reaction solution is then evaporated to dryness in a vacuum. The residue which has been taken up in ethyl acetate is washed 5 times with water, dried over magnesium sulphate and again evaporated to dryness. The residue is taken up in 30 cc of chloroform, 6 cc of 5.8 N hydrochloric acid in ether are added while cooling with ice, whereupon the solvent is removed in a vacuum and the foamy residue is digested carefully thrice with absolute ether. The ether is discarded. After this purification the hydrochloride is homogeneous in accordance with thin layer chromatography (silica gel G. chloroform/methanol 1:2).

EXAMPLE 8:
14-Desoxy-14-[(2-di-n-butylaminoethyl)mercaptoacetoxy]mutilin [process a)]

1.80 g of di-n-butylaminoethanethiol are reacted with 0.35 g of sodium in 25 cc of absolute ethanol and 5.33 g of 14-desoxy-14-tosyloxyacetoxymutilin in 15 cc of ethylmethyl ketone in a manner analogous to that described in Example 6, and conversion into the hydrochloride is effected. This is taken up in 15 cc of methanol, poured into 100 cc of water and subsequently extracted 5 times with a total of 100 cc of ether. After filtration the aqueous solution is concentrated by evaporation in a vacuum at a bath temperature of approximately 30°. The product is homogeneous in the thin layer chromatogram (silica gel G, benzene/ethyl acetate 2:1 and chloroform/methanol 1:2) and after drying in a vacuum has a softening point of 85°-90°.

EXAMPLE 9:
14-Desoxy-14-[2-(hexahydro-1H-azepin-1-yl) ethylmercaptoacetoxy]mutilin [process a)]

1.60 g of 2-(hexahydro-1H-azepinyl) ethanethiol are reacted with 0.35 g of sodium in 25 cc of absolute ethanol and 5.33 g of 14-desoxy-14-tosyloxyacetoxymutilin in 15 cc of ethylmethyl ketone in a manner analogous to that described in Example 8, and conversion into the hydrochloride is effected. Purification is effected by taking up in 15 cc of methanol, diluting with 100 cc of water and extracting 5 times with 100 cc amounts of ether. Concentration of the aqueous hydrochloride solution by evaporation at a bath temperature of 30° yields the pure hydrochloride in the form of a white powder. Softening point 110°-120°.

EXAMPLE 10:
14-Desoxy-14-{[2-(4-methyl)piperazino]ethylmercaptoacetoxy}mutilin [process a)]

4.24 g of 14-desoxy-14-tosyloxyacetoxymutilin, dissolved in 12 cc of ethylmethyl ketone, are added dropwise in an atmosphere of nitrogen to a solution of 1.22 g of (4-methylpiperazino)ethanethiol and 0.28 g of sodium in 20 cc of absolute ethanol, and the mixture is stirred at room temperature for 4 hours. The solvent is subsequently removed in a vacuum, the residue is taken up in ethyl acetate and extraction is effected thrice with water. The ethyl acetate solution is extracted thrice with 20 cc amounts of 2 N hydrochloric acid, the aqueous phase is made alkaline with a 6 N sodium hydroxide solution while cooling, and the liberated base is extracted with ethyl acetate. The solution which has been dried over magnesium sulphate is evaporated, whereby the free base is obtained and is converted into the dihydrochloride in a manner analogous to that described in Example 9. The crystalline dihydrochloride has a M.P. of 185°-188°. 1 g of crude 14-desoxy-14-{[2-(4-methyl)-piperazino]ethyl-mercaptoacetoxy}mutilin is dissolved in 10 ml dichloromethane and mixed with a solution of 0.50 g fumaric acid in warmed methanol. On addition of portions of ether the bis-hydrogen fumarate precipitates. After suction filtration, washing and drying (at 40° C over silica gel and under vacuum) the product has a melting point from 170° to 176° C.

EXAMPLE 11:
14-Desoxy-14-{[(2-hydroxyethyl)piperazino]ethylmercaptoacetoxy}mutilin [process a)]

1.81 g of (4-hydroxyethylpiperazino) ethanethiol are added to a solution of 0.35 g of sodium in 25 cc of absolute ethanol in an atmosphere of nitrogen, wherupon a solution of 5.35 g of 14-desoxy-14-tosyloxyacetoxymutilin in 15 cc of ethylmethyl ketone is added dropwise. After stirring at room temperature for 4 hours, the solvent is removed in a vacuum, the residue is taken up in 50 cc of methylene chloride, washed 5 times with water and dried over magnesium sulphate. 5 cc of 5.8 N hydrochloric acid in ether are added to the solution, and upon adding a further amount of ether the hydrochloride precipitates in crystalline form. Softening point 192°-197°.

5.50 g of the crude base of the title compound are taken up in 80 cc of absolute dichloromethane, and a solution of 2.40 g of maleic acid in 15 cc of absolute methanol is added. Absolute ether is slowly added, whereby the bis(hydrogen maleate) precipitates in crystalline form; it is filtered with suction and washed with ether. The bis(hydrogen maleate) has a M.P. of 137°-139°.

EXAMPLE 12:
14-Desoxy-14-[(2-dimethylaminoethyl)mercaptoacetoxy]mercaptoacetoxy]dihydromutilin [process a)]

The process is effected as described in Example 6, and 60 g of 14-desoxy-14-tosyloxyacetoxydihydromutilin, 7 g of sodium and 13.5 g of dimethylaminoethanethiol hydrochloride are reacted.

The trimethyl ammonium iodide is produced from the base in a manner analogous to that described in Example 1. Softening point 123°–128°.

The trimethyl ammonium chloride may be obtained from the trimethyl ammonium iodide in a manner analogous to that described in Example 1.

EXAMPLE 13:
14-Desoxy-14-[3-(diethylaminoethylmercapto)phenylmercaptoacetoxy]mutilin [process a)]

0.40 g of 3-(diethylaminoethylmercapto) thiophenol are dissolved in a solution of 37 mg of sodium in 10 cc of absolute ethanol in an atmosphere of nitrogen; 1.02 g of 14-desoxy-14-tosyloxyacetoxymutilin, dissolved in 10 cc of ethylmethyl ketone, are then added dropwise. The mixture is stirred at room temperature for 3 hours and is boiled at reflux for 1 hour. The solvent is subsequently removed by evaporation in a vacuum, the residue is taken up in ethyl acetate, and extraction is effected thrice with water. The ethyl acetate solution, which has been dried over magnesium sulphate, is concentrated by evaporation, taken up in a small amount of chloroform, a small excess of hydrochloric acid in ether is added, and concentration by evaporation is again effected. After taking up the residue in a small amount of ethanol, dilution is effected with water and extraction is effected 4 times with ether. The filtered aqueous solution is finally concentrated by evaporation in a vacuum at 30° and yields a glassy hydrochloride.

EXAMPLE 14:
14-Desoxy-14-[(2-pyrrolidinoethyl)mercaptoacetoxy]-mutilin [process a)]

5.33 g of 14-desoxy-14-tosyloxyacetoxymutilin, dissolved in 15 cc of ethylmethyl ketone, are added dropwise to a solution of 1.26 g of pyrrolidinoethanethiol and 0.35 g of sodium in 25 cc of absolute ethanol in an atmosphere of nitrogen. The reaction mixture is stirred at room temperature for 4 hours. The solvent is subsequently removed in a vacuum, and working up is effected in a manner analogous to that described in Example 6.

EXAMPLE 15:
14-Desoxy-14-[(3-dimethylaminopropyl)mercaptoacetoxy]mutilin [process a)]

2.14 g of 14-desoxy-14-tosyloxyacetoxymutilin are dissolved in 10 cc of ethylmethyl ketone, and the solution is added dropwise to a previously prepared solution of 0.48 g of 3-dimethylaminopropylmercaptan and 0.14 g of sodium in 10 cc of absolute ethanol in an atmosphere of nitrogen. The mixture is stirred at room temperature over night, the solvent is removed working up is effected as described in Example 6, and purification is effected by extracting the aqueous hydrochloride solution with ether.

A white pulverulent hydrochloride is obtained.

EXAMPLE 16 [process a)]

The following compounds may be obtained in a manner analogous to that described in the previous Examples with the use of the corresponding amounts of the appropriate starting materials:
  (a) 14-desoxy-14-[(2-di-n-butylaminopropyl)mercaptoacetoxy] mutilin, the hydrochloride of which has a softening point of 45°–48°;
  (b) 14-desoxy-14-[(2-di-n-butylaminoethyl)mercaptoacetoxy]dihydromutilin, the hydrochloride of which has a softening point of approximately 90°;
  (c) 14-desoxy-14-{[2-di-(2-ethylhexyl)aminoethyl]-mercaptoacetoxy}mutilin, the hydrochloride of which has a softening point of approximately 60°;
  (d) 14-desoxy-14-[(2-thiomorpholinoethyl)mercaptoacetoxy]mutilin, the hydrochloride of which has a softening point of 120°–125°;
  (e) 14-desoxy-14-{[2-(4-methyl)piperazino]ethylmercaptoacetoxy}dihydromutilin, the crystalline dihydrochloride of which has a M.P. of 220°–225°;
  (f) 14-desoxy-14-{[(2-hydroxyethyl)piperazino]ethylmercaptoacetoxy}dihydromutilin, the dihydrochloride of which has a softening point of 135°–140°.

EXAMPLE 17:
14-Desoxy-3-morpholino-propylamine di(acetic acid 14-mutilyl ester) [process b)]

5.33 g of 14-desoxy-14-tosyloxyacetoxymutilin are dissolved while heating in 25 cc of ethylmethyl ketone, and the solution is slowly added dropwise to a boiling mixture of 1.44 g of 3-morpholinopropylamine and 1.55 g of triethylamine. The reaction mixture is boiled at reflux for 12 hours, is subsequently concentrated by evaporation in a vacuum, the residue is taken up in ethyl acetate and the basic portions are extracted therefrom with 2 N hydrochloric acid. The bases are again liberated from the acid aqueous solution with sodium hydroxide and are taken up in ethyl acetate. After drying over sodium sulphate and concentrating by evaporation, the residue is separated chromatographically. Silica gel having a grain size of 0.05 to 0.2 mm is used as adsorbent, and methanol/chloroform (2:1) as eluant. This chromatographic separation yields two primary fractions; the material which migrates more rapidly was identified as the title compound by spectroscopic and analytic examination. The dihydrochloride has a softening point of 165°.

EXAMPLE 18:
14-Desoxy-14-[(3-morpholinopropyl)aminoacetoxy]-mutilin [process b)]

The process is effected as described in Example 17. The fraction which migrates more slowly during chromatographic separation was characterized as the title compound. The dihydrochloride has a softening point of 190°.

EXAMPLE 19:
14-Desoxy-14-[(2-diethylaminoethyl) aminoacetoxy]-mutilin [process b)]

2.12 g of 14-desoxy-14-tosyloxyacetoxymutilin are dissolved in 10 cc of warm ethylmethyl ketone, the solution is added dropwise to a boiling mixture of 0.98 g of diethylaminoethylamine and 0.60 g of triethylamine, as described in Example 17, and the mixture is boiled at reflux for 7 hours. Isolation of the base is effected as described in Examples 1, 2 and 17. Crystals having a M.P. of 108°–112° are obtained. The dihydrochloride, which can be obtained using hydrochloric acid in methanol, has a softening point of 150°.

EXAMPLE 20:
14-Desoxy-14-(4-hydroxyethylpiperazinoacetoxy)mutilin [process b)]

0.50 g of N-hydroxyethylpiperazine and 0.60 g of triethylamine are dissolved in 5 cc of absolute ethanol, whereupon a solution of 2.12 g of 14-desoxy-14-tosyloxyacetoxymutilin in 10 cc of ethylmethyl ketone is added dropwise in an atmosphere of nitrogen, and the reaction solution is subsequently boiled at reflux for 6 hours. The solvent is subsequently removed in a vacuum, and working up is effected as described in Example 10. The dihydrochloride has a M.P. of 133°–137°.

EXAMPLE 21:
14-Desoxy-14-[4-(2-dimethylaminoethoxy)phenylmercapto]acetoxymutilin [process c)]

100 mg of 14-desoxy-14-(4-hydroxyphenylmercapto)acetoxymutilin are dissolved in 10 cc of ethylmethyl ketone, and after the addition of 30 mg of dimethylaminoethyl chloride hydrochloride, 150 mg of finely pulverized dry potassium carbonate and 30 mg of potassium iodide, the mixture is boiled at reflux for 11 hours. The solvent is subsequently removed by distillation, the residue is taken up in ethyl acetate, washed thrice with water, dried over sodium sulphate and concentrated by evaporation. Isolation is effected by preparative thin layer chromatography on silica gel with chloroform/methanol (1:2) as eluant.

EXAMPLE 22:
14-Desoxy-14-[4-(3-dimethylaminopropoxy)phenylmercapto]acetoxymutilin [process c)]

100 mg of 14-desoxy-4-(4-hydroxyphenylmercapto)acetoxymutilin are dissolved in 3 cc of ethylmethyl ketone, 55 mg of sodium methoxide in 2 cc of methanol are first added, and then 35 mg of 3-dimethylaminopropyl chloride hydrochloride are added. The mixture is stirred at room temperature in an atmosphere of nitrogen for 3 hours and is then boiled at reflux for 14 hours. After removing the solvent by evaporation, the residue is taken up in ethyl acetate, washed thrice with water, dried over sodium sulphate and concentrated by evaporation. Purification is effected by thin layer chromatography on silica gel with chloroform/methanol (1:2) as eluant.

EXAMPLE 23:
14-Desoxy-14-[4-(2-diethylaminoethoxy)phenylmercapto]acetoxymutilin [process c)]

960 mg of 14-desoxy-14-(4-hydroxyphenyl-mercapto)acetoxymutilin are dissolved in 20 cc of absolute methanol, 120 mg of sodium methoxide are subsequently added, and the mixture is evaporated to dryness in a vacuum. The evaporation residue is taken up in a mixture of 4 cc of water and 20 cc of xylene, 360 mg of diethylaminoethyl chloride hydrochloride and 420 mg of potassium carbonate are added, and the mixture is heated at reflux at a bath temperature of 150° for 8 hours. The xylene layer is subsequently washed 5 times with water, the combined aqueous phases are extracted once with ethyl acetate, and the combined organic phases are concentrated by evaporation in a vacuum. The residue is dissolved in 10 cc of methylene chloride and is converted into the hydrochloride with 0.6 cc of 5.8 N hydrochloric acid in ether. After removing the solvent in a vacuum, the hydrochloride is dissolved in 6 cc of methanol, diluted with 30 cc of distilled water and subsequently extracted 6 times with a total of 80 cc of ether. The purified aqueous solution of the hydrochloride is concentrated by evaporation in a vacuum at a bath temperature of approximately 30°. The compound is homogeneous in accordance with thin layer chromatography on silica gel G in the system chloroform/methanol (1:2). The foamy product is dried in a vacuum over potassium hydroxide.

EXAMPLE 24:
14-Desoxy-14-[3-dimethylaminoethylmercapto)phenylmercapto]acetoxymutilin [process c)]

0.57 g of dithioresorcin are dissolved in a solution of 46 mg of sodium in 5 cc of absolute ethanol in an atmosphere of nitrogen. A solution of 1.59 g of 14-desoxy-14-tosyloxyacetoxymutilin in 10 cc of ethylmethyl ketone is then added dropwise while stirring. After stirring for 2 hours at room temperature, the reaction mixture is evaporated to dryness in a vacuum. The residue is taken up in ethyl acetate, washed with water, dried over magnesium sulphate and concentrated by evaporation. The crude product is taken up in a solution of 74 mg of sodium in 15 cc of absolute ethanol, and after the addition of 0.94 g of dimethylaminoethyl chloride hydrochloride, the mixture is heated at reflux for 5 hours. The solvent is then removed in a vacuum and the residue is chromatographed on a silica gel column (grain size 0.05 to 0.2 mm) with a mixture of chloroform/methanol (1:2).

EXAMPLE 25 [process c)]

The following compounds may be obtained in a manner analogous to that described in Example 23, using the corresponding amounts of the appropriate starting materials:

(a) 14-desoxy-14-{4-[3-(N-piperidino) propoxy]phenylmercapto}acetoxymutilin;

(b) 14-desoxy-14-[4-(2-diethylaminoethoxy)phenylmercapto]acetoxy-dihydromutilin;

(c) 14-desoxy-14-[2-(2-diethylaminoethoxy)phenylmercapto]acetoxymutilin.

EXAMPLE 26:
14-Desoxy-14-{[2-(4-acetoxyethyl)piperazino]ethylmercaptoacetoxy}mutilin [process d)]

1.81 g of (4-hydroxyethyl-piperazino) ethanethiol are added to a solution of 0.35 g of sodium in 25 cc of absolute ethanol in an atmosphere of nitrogen, and a solution of 5.35 g of 14-desoxy-14-tosyloxyacetoxymutilin in 15 cc of ethylmethyl ketone is then added dropwise. After stirring at room temperature for 4 hours, the solvent is removed in a vacuum, the residue is taken up in 50 cc of ethyl acetate, whereby a partial interchange of ester radicals occurs. Separation of the acetylated from the non-acetylated product is effected by column chromatography on silica gel with chloroform/methanol (7:1) as eluant. The fraction which migrates more rapidly is converted into the hydrochloride with hydrochloric acid in ether. Softening point 137°–140°.

The bis(hydrogen maleate) is produced in a manner analogous to that described in Example 11. M.P. 142°–144°.

EXAMPLE 27:
14-Desoxy-14-{[2-(4-acetoxyethyl)piperazino]ethylmercaptoacetoxy}mutilin [process d)]

10 cc of acetic anhydride are added to 4.0 g of 14-desoxy-14-{[2-(4-hydroxyethyl)piperazino]ethylmercaptoacetoxy}mutilin while cooling with ice, and the mixture is subsequently stirred at room temperature for 5 hours. The mixture is then poured into 150 cc of cold water, is stirred for 1 hour and extracted thrice with ether. The ether phases are discarded, and the water phase is made alkaline with a 10 N aqueous sodium hydroxide solution while cooling. The precipitated free base is taken up in ethyl acetate. After drying the solution over magnesium sulphate and removing the solvent by evaporation, the pure base is obtained.

EXAMPLE 28:
14-Desoxy-14-{[2-(4-propionyloxyethyl)piperazino]ethylmercaptoacetoxy}mutilin [process d)]

0.05 g of 14-desoxy-14-{[2-(4-hydroxyethyl)piperazino]ethylmercaptoacetoxy}mutilin are boiled at reflux in 5 cc of dichloromethane with 0.20 g of propionyl chloride for 2 hours. After cooling, the crystalline dihydrochloride is precipitated by the addition of hydrochloric acid in ether and dilution with absolute ether. The salt is filtered with suction and washed with ether. M.P. 182°–187°.

EXAMPLE 29:
14-Desoxy-14-{[2-(4-pivaloyloxyethyl)piperazino]ethylmercaptoacetoxy}mutilin [process d)]

0.50 g of 14-desoxy-14-{[2-(4-hydroxyethyl)piperazino]ethylmercaptoacetoxy}mutilin are boiled at reflux in 5 cc of dichloromethane with 0.15 g of pivaloyl chloride for 4 hours. After cooling, the crystalline dihydrochloride precipitates by the addition of hydrochloric acid in ether and dilution with absolute ether. After filtering with suction, the dihydrochloride is washed with absolute ether for a short time and is dried in a vacuum. The compound hydrolyzes very readily to the starting material in the presence of water.

EXAMPLE 30:
14-Desoxy-14-{[2-(4-benzoyloxyethyl)piperazino]ethylmercaptacetoxy}mutilin [process d)]

0.50 g of 14-desoxy-14{[2-(4-hydroxyethyl)piperazino]ethylmercaptoacetoxy}mutilin are allowed to react in a manner analogous to that described in Examples 28 and 29 with 0.16 g of benzoyl chloride. The dihydrochloride is subsequently precipitated as described. Softening point 132°–135°.

EXAMPLE 31:
14-Desoxy-14-{[2-(4-acetoxyethyl)piperazino]ethylmercaptoacetoxy}dihydromutilin [process d)]

0.50 g of 14-desoxy-14-{[2-(4-hydroxyethyl)piperazino]ethylmercaptoacetoxy}dihydromutilin are allowed to stand with 1.5 cc of acetic anhydride at rooom temperature for 2 hours, dilution is subsequently effected with 10 cc of water, and the mixture is stirred at room temperature for 1 hour in order to decompose the excess acetic anhydride. The solution is extracted thrice with ether. The dihydrochloride is precipitated from the concentrated solution with hydrochloric acid in ether, as described in Example 29. M.P. 133°–135°.

PRODUCTION OF THE STARTING MATERIALS

EXAMPLE 32:
14-Desoxy-14-tosvloxyacetoxy-dihydromutilin (for Examples 3, 12, 16b, 16e, 16f and 35)

6.10 g of p-toluenesulphochloride are added at once with vigorous stirring to a solution of 8.86 g of dihydropleuromutilin in 30 cc of dry pyridine at −15°; stirring is effected at −15° for 2 hours, and then at 0° for 1 hour. The mixture is then poured on ice water, and the product is taken up in methylene chloride. The organic phase is successively washed with ice water and with saturated sodium hydrogen carbonate solution while cooling. Drying over sodium sulphate and evaporation yield a thin layer chromatographically homogeneous product having a softening point of 78°–80°.

EXAMPLE 33:
14-Desoxy-14-tosyloxyacetoxy-dihydromutilin (for Examples 3, 12, 16b, 16e, 16f and 35)

0.53 g of 14-desoxy-14-tosyloxyacetoxymutilin are hydrogenated in 10 cc of ethyl acetate with 0.10 g of 10% palladium charcoal as catalyst, at atmospheric pressure and room temperature. The calculated amount of hydrogen is taken up after approximately one hour. The catalyst is removed from the solution by filtration, and the solution is concentrated by evaporation in a vacuum. Softening point 78°–80°.

EXAMPLE 34:
3-(Diethylaminoethylmercapto)thiophenol (for Example 13)

A solution of 1.72 g of diethylaminoethyl chloride hydrochloride and 0.54 g of sodium methoxide in 10 cc of methanol and a solution of 2.09 g of potassium carbonate in 10 cc of water are added to 1.42 g of dithioresorcin. After the addition of 10 cc of xylene, the mixture is boiled at reflux for 8 hours. The reaction mixture is subsequently diluted with water and extracted thrice with ethyl acetate. 10% acetic acid is subsequently added to the water phase, until the oily precipitation is complete, extraction is again effected thrice with ethyl acetate, and the ethyl acetate solution is concentrated by evaporation after drying over magnesium sulphate. Bulb tube distillation (bath temperature 135° at 0.5 mm Hg) yields the product as colourless oil which rapidly oxidizes in the air.

EXAMPLE 35:
14-Desoxy-14-(4-hydroxyphenylmercapto)acetoxydihydromutilin (for Example 25b)

6.00 g of 14-desoxy-14-tosyloxyacetoxy-dihydromutilin are dissolved in 15 cc of ethylmethyl ketone. 1.60 g of thiohydroquinone are added to this solution in an atmosphere of nitrogen. A solution of 0.35 g of sodium in 25 cc of absolute ethanol is then added dropwise while cooling with ice and stirring, whereupon stirring is continued at room temperature for 5 hours. Working up is effected by acidifying the reaction mixture with 10% acetic acid (pH 4.5) and subsequently concentrating by evaporation in a vacuum. The residue is taken up in ethyl acetate, water is added and extraction is effected 4 times with ethyl acetate. The combined organic phases are washed once with water, dried over sodium sulphate and concentrated by evaporation in a vacuum. The compound crystallizes from chloroform/hexane and has a M.P. of 191°–194°.

EXAMPLE 36:
14-Desoxy-14-(2-hydroxyphenylmercapto)acetoxymutilin (for Example 25c)

5.33 g of 14-desoxy-14-tosyloxyacetoxymutilin are reacted with 1.57 g of 2-mercaptophenol and 0.25 g of sodium in 10 cc of absolute ethanol, as described in Example 35, and working up is effected in analogous manner. The compound crystallizes from chloroform and has a M.P. of 150°–152°.

EXAMPLE 37:
Pyrrolidinoethanethiol (for Example 14)

A solution of 42.67 g of pyrrolidine (distilled over potassium hydroxide) in 75 cc of absolute toluene is boiled at reflux (a trap cooled with dry ice/acetone is placed on the reflux condenser), whereby 30.04 g of ethyl-2-mercaptoethyl carbonate are added dropwise within 1 hour while stirring. The mixture is kept at the boil for a total of 8 hours. The solvent is then removed in a vacuum, and the residue is distilled over a Vigreux column. B. P. 60°–63°/7 mm Hg. $n_D^{20} = 1.50008$.

EXAMPLE 38:
Starting mateirals of formula IV (for Examples 9, 11, 16c, 16d and 16f)

A solution of ethylene sulphide in benzene is heated in an autoclave to 100° with a molar excess of a corresponding secondary amine. After cooling the reaction mixture, the polymeric material is filtered off, washing is effected with benzene, the solvent is removed by evaporation and the product is distilled over a Vigreux column.

TABLE

| Molar ratio amine/ethylene sulphide | Reaction time | Compounds of formula IV | B.P./mm Hg |
|---|---|---|---|
| 3 : 1 | 17 hours | 2-[N,N-Bis-(2-ethylhexyl)amino]ethanethiol | 105–107°/0.2 |
| 3 : 1 | 17 hours | (4-Hydroxyethyl-piperazino)ethanethiol | 97.5°/0.1 |
| 4 : 1 | 22 hours | (2-Morpholino)ethanethiol | 46–47°/5 |
| 6 : 1 | 21 hours | (Hexahydro-1H-azepinyl)ethanethiol | 55.5°/0.6 |

What is claimed is:

1. A compound of the formula:

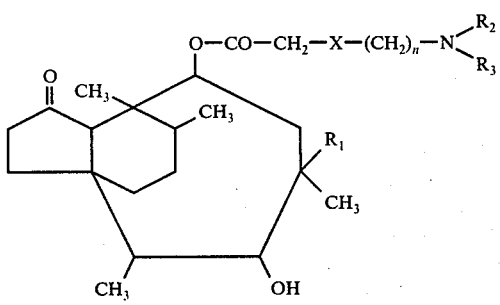

wherein
either
  $R_1$ is ethyl or vinyl,
  $n$ is an integer from 2 to 5,
  X is sulphur
  a group

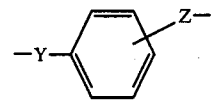

or a group $=N-R_4'$,
wherein
  either Y and Z are both sulphur, or
  one of Y and Z is oxygen and the other is sulphur, and
  $R_4'$ is hydrogen or a group of the formula:

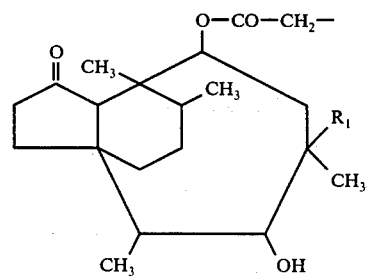

wherein
  $R_1$ is as defined above,
  $R_2$ and $R_3$ together with the nitrogen atom form a piperazinyl radical, the second nitrogen atom of which is substituted by alkyl of 1 to 5 carbon atoms or hydroxyalkyl of 1 to 4 carbon atoms (alkancyloxy of 2 to 5 carbon atoms) alkyl of 1 to 4 carbon atoms or (benzoyloxy) alkyl of 1 to 4 carbon atoms,
or wherein
  $R_1$ is as defined above,
  $n$ is the number 2,
  $R_3$ is alkyl of 1 to 10 carbon atoms, hydroxyalkyl of 1 to 4 carbon atoms, (alkanoyloxy of 2 to 5 carbon atoms) alkyl of 1 to 4 carbon atoms or (benzoyloxy) alkyl of 1 to 4 carbon atoms,
  X is the group $=N-R_4^{II}$, and
  $R_2$ together with $R_4^{II}$ forms an ethylene bridge between both nitrogen atoms,
and pharmaceutically acceptable acid addition salts and quaternary salts thereof.

2. A compound of claim 1, in which X is sulphur.

3. A compound of claim 2, in which $n$ is 2 or 3, and $R_2$ and $R_3$, together with the nitrogen atom to which they are attached, signify, 4-alkylpiperazino, in which the alkyl radical contains 1 to 3 carbon atoms, or 4-hydroxyethylpiperazino.

4. A compound of claim 2, in which $R_2$ and $R_3$ together with the nitrogen atom to which they are attached form a piperazinyl radical, the second nitrogen atom of which is substituted by $(C_{2-5})$ alkanoyloxy $(C_{1-4})$alkyl or benzoyloxy $(C_{1-4})$alkyl.

5. A compound of claim 4, in which n is 2 or 3, and $R_2$ and $R_3$, together with the nitrogen atom to which they are attached signify 4-acetoxyethylpiperazinyl or 4-benzoyloxyethylpiperazinyl.

6. A compound of claim 1, in which X is the radical

in which either Y and Z are both sulphur,
or one of Y and Z is sulphur and the other is oxygen.

7. A compound of claim 6, in which Y is sulphur.

8. A compound of claim 7, in which n is 2 or 3, and $R_2$ and $R_3$, together with the nitrogen atom to which they are attached, signify 4-alkylpiperazino, in which the alkyl radical contains 1 to 3 carbon atoms, or 4-hydroxyethylpiperazino.

9. A compound of claim 7, in which $R_2$ and $R_3$, together with the nitrogen atom to which they are attached form a piperazinyl radical, the second nitrogen atom of which is substituted by $(C_{2-5})$alkanoyloxy $(C_{1-4})$alkyl or benzoyloxy$(C_{1-4})$alkyl.

10. A compound of claim 9, in which n is 2 or 3, and $R_2$ and $R_3$, together with the nitrogen atom to which they are attached signify 4-acetoxyethylpiperazinyl or 4-benzoyloxyethylpiperazinyl.

11. A compound of claim 1, in which X is the group $=N-R_4'$, in which $R_4'$ is as defined in claim 1.

12. A compound of claim 11, in which X is -NH-.

13. A compound of claim 11, in which n is 2 or 3, and $R_2$ and $R_3$, together with the nitrogen atom to which they are attached, signify 4-alkylpiperazino, in which the alkyl radical contains 1 to 3 carbon atoms, or 4-hydroxyethylpiperazino.

14. A compound of claim 12, in which $R_2$ and $R_3$, together with the nitrogen atom to which they are attached form a piperazinyl radical, the second nitrogen atom of which is substituted by $(C_{2-5})$alkanoyloxy$(C_{1-4})$alkyl or benzoyloxy$(C_{1-4})$alkyl.

15. A compound of claim 14, in which n is 2 or 3, and $R_2$ and $R_3$, together with the nitrogen atom to which they are attached signify 4-acetoxyethylpiperazinyl or 4-benzoyloxyethylpiperazinyl.

16. A compound of claim 11, in which X is the group

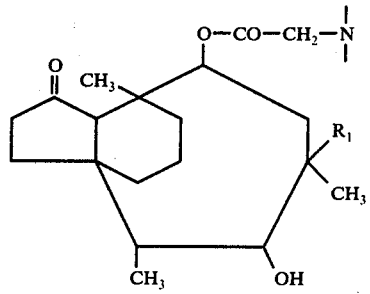

17. A compund of claim 16, in which n is 2 or 3, and $R_2$ and $R_3$, together with the nitrogen atom to which they are attached, signify 4-alkyl-piperazino, in which the alkyl radical contains 1 to 3 carbon atoms or 4-hydroxyethylpiperazino.

18. A compund of claim 16 in which $R_2$ and $R_3$, together with the nitrogen atom to which they are attached form a piperazinyl radical, the second nitrogen atom of which is substituted by $(C_{2-5})$alkanoyloxy$(C_{1-4})$alkyl or benzoyloxy$(C_{1-4})$alkyl.

19. A compound of claim 18, in which n is 2 or 3, and $R_2$ and $R_3$, together with the nitrogen atom to which they are attached signify 4-acetoxyethylpiperazinyl or 4-benzoyloxyethylpiperazinyl.

20. A compound of claim 1, in which n is 2, $R_3$ is alkyl of 1 to 10 carbon atom, hydroxyalkyl of 1 to 4 carbon atoms, $(C_{2-5})$alkanoyloxy$(C_{1-4})$alkyl, or benzoyloxy $(C_{1-4})$alkyl, X is the group $=N-R_4''$, and $R_2$ together with $R_4''$ forms an ethylene bridge between the two nitrogen atoms.

21. A compound of claim 20, in which $R_3$ is alkyl of 1 to 8 carbon atoms, acetoxyethyl or benzoyloxyethyl.

22. The compound of claim 1, which is 14-Desoxy-14-{[2-(4-methyl)piperazino]ethylmercaptoacetoxy}mutilin.

23. The compound of claim 1, which is 14-Desoxy-14-{[(2-hydroxyethyl)piperazino]ethylmercaptoacetoxy}mutilin.

24. The compound of claim 1, which is 14-Desoxy-14-{[2-(4-methyl)piperazino]ethylmercaptoacetoxy}dihydromutilin.

25. The compound of claim 1, which is 14-Desoxy-14-{[(2-hydroxyethyl)piperazino]ethylmercaptoacetoxy}dihydromutilin.

26. The compound of claim 1, which is 14-Desoxy-14-(4-hydroxyethylpiperazinoacetoxy)-mutilin.

27. The compound of claim 1, which is 14-Desoxy---{[2-(4-acetoxyethyl)piperazino]ethylmercaptoacetoxy}mutilin.

28. The compound of claim 1, which is 14-Desoxy-14-{[2-(4-propionyloxyethyl)-piperazino]ethylmercaptoacetoxy}mutilin.

29. The compound of claim 1, which is 14-Desoxy-14-{[2-(4-pivaloxyloxyethyl)piperazino]ethylmercaptoacetoxy}mutilin.

30. The compound of claim 1, which is 14-Desoxy-14-{[2-(4-benzoyloxyethyl)piperazino]ethylmercaptoacetoxy}mutilin.

31. The compound of claim 1, which is 14-Desoxy-14-{[2-(4-acetoxyethyl)piperazino]ethylmercaptoacetoxy}dihydromutilin.

\* \* \* \* \*